United States Patent
Suckeveriene et al.

(10) Patent No.: US 12,250,959 B2
(45) Date of Patent: Mar. 18, 2025

(54) COMPOSITIONS FOR WEIGHT MANAGEMENT

(71) Applicant: OBVISLIM LTD, Kfar Baruch (IL)

(72) Inventors: Ran Yosef Suckeveriene, Haifa (IL); Itai Shmuel Tzchori, Kfar Yehoshua (IL); Boris Rozenblit, Haifa (IL)

(73) Assignee: CALEE SCIENTIFIC TECHNOLOGIES LTD., Yokneam (IL)

( * ) Notice: Subject to any disclaimer, the term of this patent is extended or adjusted under 35 U.S.C. 154(b) by 656 days.

(21) Appl. No.: 17/298,659

(22) PCT Filed: Dec. 1, 2019

(86) PCT No.: PCT/IL2019/051318
§ 371 (c)(1),
(2) Date: May 31, 2021

(87) PCT Pub. No.: WO2020/115738
PCT Pub. Date: Jun. 11, 2020

(65) Prior Publication Data
US 2022/0046972 A1    Feb. 17, 2022

Related U.S. Application Data

(60) Provisional application No. 62/774,270, filed on Dec. 2, 2018.

(51) Int. Cl.
*A23L 33/24* (2016.01)
*A23L 33/25* (2016.01)
*A23L 33/28* (2016.01)

(52) U.S. Cl.
CPC ............... *A23L 33/24* (2016.08); *A23L 33/25* (2016.08); *A23L 33/28* (2016.08)

(58) Field of Classification Search
CPC ........... A23L 33/24; A23L 33/25; A23L 33/28
See application file for complete search history.

(56) References Cited

U.S. PATENT DOCUMENTS

| | | |
|---|---|---|
| 11,090,354 B2 | 8/2021 | Jozefiak et al. |
| 2016/0022729 A1 | 1/2016 | Karp et al. |
| 2016/0354509 A1* | 12/2016 | Parlato .................... A61L 24/04 |
| 2017/0258824 A1 | 9/2017 | Vetter |
| 2018/0228863 A1* | 8/2018 | Jozefiak ................. A61K 38/02 |

FOREIGN PATENT DOCUMENTS

WO    2017/053970 A1    3/2017

OTHER PUBLICATIONS

Ikbel Benalaya et al, A Review of Natural Polysaccharides: Sources, Characteristics, Properties, Food, and Pharmaceutical Applications, Int. J. Mol. Sci. 2024, 25, 1322 (Year: 2024).*
International Search Report for PCT/IL2019/051318, mailed Feb. 6, 2020 (3 pages).
Written Opinion of the International Searching Authority for PCT/IL2019/051318, mailed Feb. 6, 2020 (5 pages).
Communication and Supplementary European Search Report for EP 19 89 2712, mailed Jul. 11, 2022 (9 pages).

* cited by examiner

*Primary Examiner* — Mark V Stevens
*Assistant Examiner* — Alparslan Asan
(74) *Attorney, Agent, or Firm* — Roach Brown McCarthy & Gruber, P.C.; Kevin D. McCarthy

(57) ABSTRACT

The invention relates to compositions and formulations for managing weight in obese persons and individuals who wish to maintain their weight in a desired value regardless of their lifestyle habits or food preferences. The compositions comprise polymeric compounds that when administered as described herein form an intestinal overlay in situ which modulates the absorption of nutrients in the intestines for certain periods of time.

14 Claims, 5 Drawing Sheets

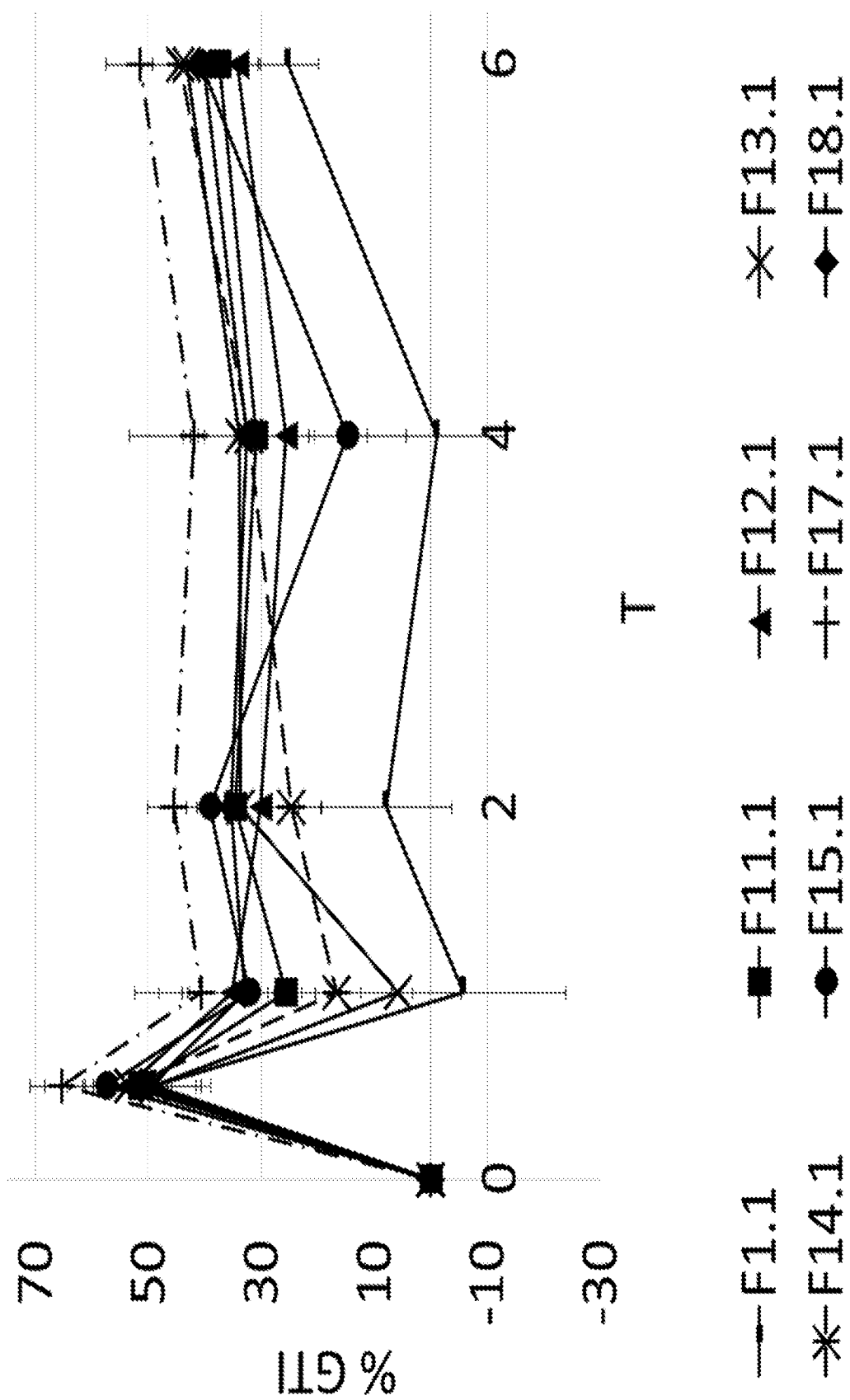

COMPOSITIONS FOR WEIGHT MANAGEMENT

FIELD OF THE INVENTION

The present invention relates to the field of nutraceutical compositions and food supplements. More particularly, the invention relates to compositions and formulations for managing weight in obese persons and individuals who wish to maintain their normal weight regardless of their lifestyle habits or food preferences. The compositions comprise polymeric components which spontaneously form an intestinal overlay in situ thereby altering the absorption of certain nutrients to improve one's lifestyle and well-being.

BACKGROUND OF THE INVENTION

Obesity is a major issue that affects large populations in developed countries. In addition to the psychosocial stigmas associated with this condition, obese individuals are presented with many complications and due to the prevalence and costs associated with managing obesity it bears a significant burden on society and the healthcare system. Interestingly however, a 5-10% reduction in one's body mass index (BMI) can help prevent obesity-related conditions and improve overall health significantly.

As such, there is an ever-growing need for innovative solutions to the weight management problem. Several methods are known in the art to reduce food absorption which typically fall into 4 broad categories: lifestyle changes, medications, surgeries, and minimally-invasive procedures.

Lifestyle changes such as dietary restriction, which is well known in the art, have proven to have a time-limited effect on a person's weight as many generally find it difficult to abide by and maintain an ideal body weight over long periods of time. On the other hand, bariatric surgeries although effective may pose a risk and are unfortunately limited to select individuals that meet the eligibility criteria which includes having a relatively high BMI. Similarly, most weight-loss medications have numerous side effects and generally have a poor long-term effect. In regards to non-surgical solutions, the intra-gastric balloon (IGB) is the most common recourse. However, it suffers from several limitations including rapid inflation and limited adjustability of the device, as well as the requirement of performing an endoscopic insertion or extraction.

Overall, many overweight or obese individuals fail to adhere to their prescribed diets due to either non-ideal food preferences or lifestyle changes, others refuse to live with the medications' undesirable side effects, while for many others surgery is prohibitively costly or risky.

As overweight or obese individuals would prefer to manage their weight without being forced to change their diet or lifestyle, for example, by restricting the types and amounts of food they consume, ideal solutions to weight reduction should not interfere with one's existing eating preferences and allow him to enjoy eating food as desired.

It is therefore an object of the present invention to provide a non-invasive, lifestyle-conforming, and affordable solution to weight management which does not pose a risk to a potential user.

It is another object of the invention to provide compositions for managing the weight of a person as well as methods of using the same.

Other objects and advantages of the invention will become apparent as the description proceeds.

SUMMARY OF THE INVENTION

According to one aspect the invention provides a composition comprising two or more barrier-forming mucoadhesive substances as active ingredients that produce an intestinal overlay when consumed by a person is disclosed herein for use in managing the weight of a person.

According to one embodiment, the composition is used for managing the weight of a person by reducing the absorption of nutrients and food particles in the gastrointestinal (GI) tract. According to a specific embodiment, the composition is used for managing the weight of the person by reducing the absorption of nutrients such as proteins, amino acids, sugars, glucose, fats, fatty acids, and lipids.

According to another embodiment, the intestinal overlay is transient and forms a temporary physical barrier which limits the absorption of nutrients and food particles in the small intestines. According to a further embodiment, the intestinal overlay remains in contact with the mucosal surface of the small intestines for a time period ranging from 15 minutes to 7 days post administration.

According to another embodiment, the composition is consumed once, or on a regular basis continuously or intermittently. According to a specific embodiment, the composition is consumed by the person before a meal.

According to a further embodiment, the composition is consumed by a person, who is an overweight person or an individual interested in attaining or maintaining a certain body weight. According to a specific embodiment, the person is one with a normal BMI that is below 25, an overweight person with a BMI that is between 25-30, and an obese person with a BMI greater than 30. According to another specific embodiment, the composition reduces the glycemic index of nutrients and food particles by at least 10% and up to 80% of the original glycemic index value.

According to still further embodiment, the barrier-forming mucoadhesive substance is selected from chitosan, alginate, carbopol, pectin, cross-linked polyacrylic acid, polyethylene glycol (PEG), carboxymethyl cellulose (CMC), hyaluronic acid (HA), hydroxy ethyl cellulose (HEC), hydroxypropyl methylcellulose (HPMC), hydroxypropyl cellulose (HPC), gum karaya, guar gum, xanthan gum, and tragacanth.

According to another aspect, the invention provides a method of managing the weight of a person comprising administering to said person an effective amount of a composition comprising one or more barrier-forming mucoadhesive substances as the active ingredients.

According to one embodiment, the method of managing the weight of a person includes reducing the absorption of nutrients and food particles in the gastrointestinal (GI) tract. According to another embodiment, the method of managing the weight of a person includes reducing the absorption of nutrients and food particles such as proteins, amino acids, sugars, glucose, fats, fatty acids, and lipids.

According to another embodiment, the method of managing the weight of a person comprises administering to said person an effective amount of a composition once, or on a regular basis continuously or intermittently, prior to consuming food. According to a specific embodiment, the composition is administered before a meal.

According to another embodiment, the method is used in managing the weight of an overweight person or an individual interested in attaining or maintaining a certain body weight. According to a specific embodiment, the method is used in managing the weight of a person with a normal BMI that is below 25, an overweight person with a BMI that is between 25-30, and an obese person with a BMI greater than 30. According to a specific embodiment, the method of managing the weight of a person conforms to a person's lifestyle or eating habits.

According to another embodiment, the method of managing the weight of a person comprises administering to said person an effective amount of a composition comprising one or more barrier-forming mucoadhesive substances that are selected from chitosan, alginate, carbopol, pectin, cross-linked polyacrylic acid, polyethylene glycol (PEG), carboxymethyl cellulose (CMC), hyaluronic acid (HA), hydroxyethyl cellulose (HEC), hydroxypropyl methylcellulose (HPMC), hydroxypropyl cellulose (HPC), gum karaya, guar gum, xanthan gum, and tragacanth.

BRIEF DESCRIPTION OF THE DRAWINGS

FIG. 3 shows percent of glucose transport inhibition (GTI) over time (T, in hours) in a side-bi-side diffusion chamber through a mucin-coated membrane further coated with the indicated barrier formulation compared to a reference mucin-coated membrane. Formulation (F) composition is as described in Table 1 below. The formulations were further subjected to homogenization (thus designated by the number of the formulation as in Table 1, with the addition of "0.1").

FIG. 4A shows blood glucose levels normalized to basal glucose levels in the blood (Glu, in mg/dL) over time (T, in minutes) in control rats (C) and in rats treated with formulation 13 (F13, as described in Table 1 below) prior to administration of glucose solution; n=3, *$p<0.05$.

FIG. 4B shows blood glucose levels normalized to basal glucose levels in the blood (Glu, in mg/dL) over time (T, in minutes) in control rats (C) and in rats treated with formulation 11 (F11, as described in Table 1 below) prior to administration of glucose solution; n=5, *$p<0.05$.

DETAILED DESCRIPTION OF THE INVENTION

Figure 1:
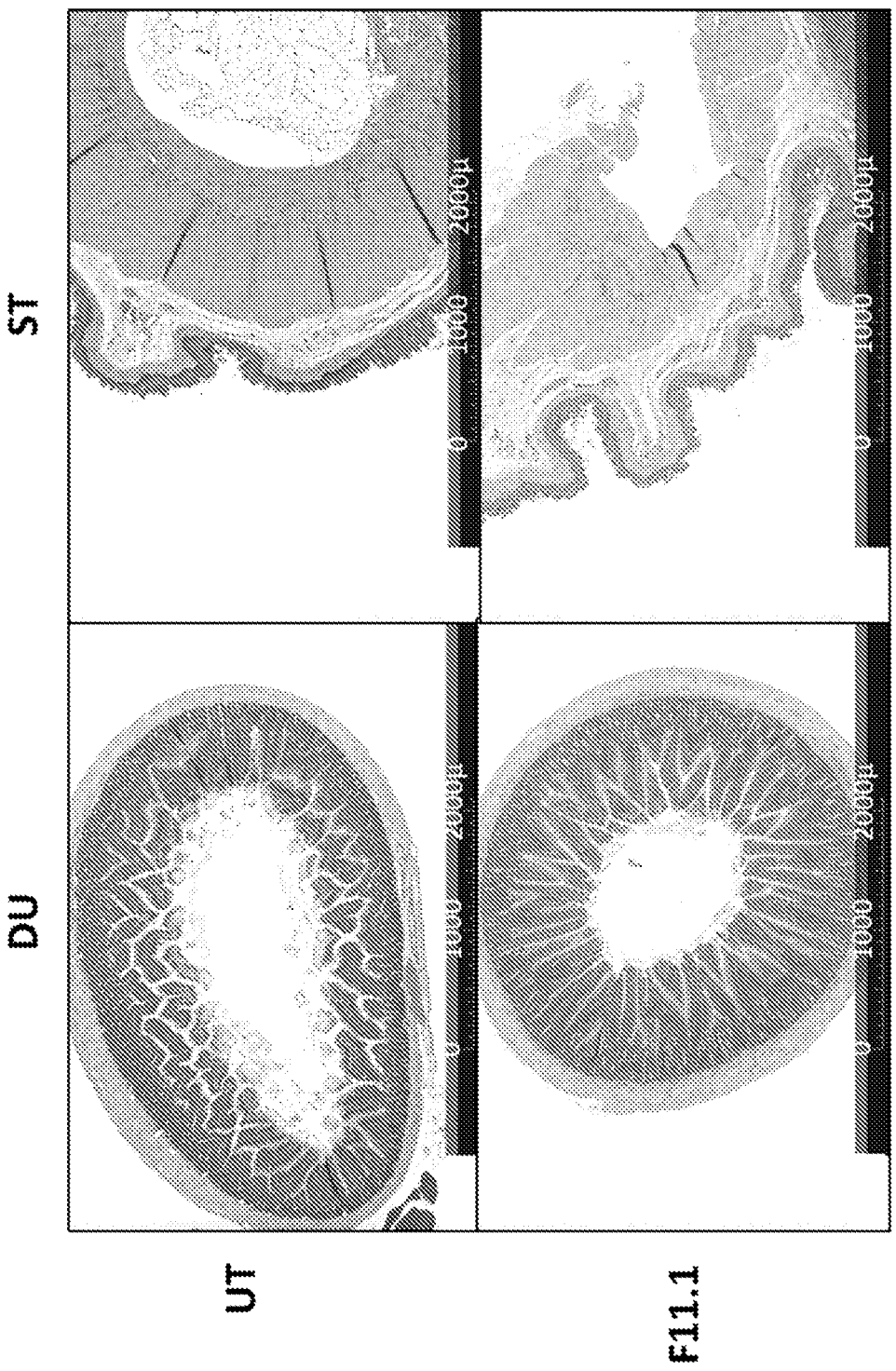
FIG. 1 shows histology sections of the stomach (ST) and duodenum (DU) of untreated rats (UT) or rats treated with a formulation comprising chitosan (1.2% w/v), HEC (0.6% w/v) and alginate (0.5% w/v), that underwent homogenization (F11.1).

The present invention provides nutraceutical compositions and formulations comprising one or more barrier-forming mucoadhesive substances that when administered as described herein coat the inner wall surface of organs in the gastrointestinal (GI) tract to form a temporary physical barrier in situ, specifically in the small intestine, for temporarily reducing nutrient absorption from the GI tract, such as from the intestine, into the blood stream. Non-limiting examples of nutrients include sugars, such as glucose, fats, fatty acids, proteins and amino acids.

The mucoadhesive substances of the compositions disclosed herein are well-known in the field of medicine such as in the preparation of pharmaceuticals, where they serve as excipients or additives that enhance the characteristics or action of the active ingredients of the medicament. Importantly, the mucoadhesive substances of the invention do not in themselves have a role in treating a particular condition, rather, these components are merely added to other compositions for administration purposes such as enteric coating that protects the active pharmaceutical ingredient (API) from degradation in GI tract, targeted delivery of the API to a specific portion of the GI tract, or in the manufacturing process of dosage forms such as in maintaining the integrity of a solid composition during the tableting process and extending the shelf-life of pharmaceutical products.

The inventors have surprisingly found that these mucoadhesive components function independently of other factors as robust active ingredients for limiting the absorption of nutrients such as glucose in the intestines thereby helping to maintain or even reduce weight gain in individuals who prefer to maintain their current diet or lifestyle, such as those who have a high fat or high carbohydrate diet.

Importantly, the inventors have serendipitously found that the mucoadhesive components when combined in a composition and administered to individuals either via a dosage regiment or a one-time basis prior to consuming food are surprisingly effective at reducing the absorption of nutrients such as glucose. As such, compositions and formulations comprising these components according to the invention are to be used as non-invasive, temporary, personalized, versatile and effective means of managing one's weight, such as but not limited to overweight persons and individuals who wish to attain or maintain a certain body weight, conforming to their current lifestyle or eating habits without the need to change them. For example, the present invention provides a composition or formulation which can be administered to a subject in need before a high calorie meal which results in the formation of an intestinal overlay that limits the absorption of nutrients and/or food particles (such as proteins, amino acids, sugars, saccharides, fats, and lipids) present in the meal for a certain period of time. Thus, the person addressed to by the invention can be one with a normal BMI that is below 25, an overweight person with a higher a BMI that is between 25-30, and an obese person with a BMI greater than 30.

Furthermore, as it appears that lowering the glycemic load of a diet is an effective way of promoting weight loss and improving lipid profiles, the present invention also provides a composition or formulation which can be administered to a subject in need before a meal having a high glycemic index, to effectively lower the glycemic index, allowing the subject to consume food as desired. In a particular embodiment, the composition or formulation of the invention, when administered to a subject, reduce the glycemic index of certain food by at least 10% and up to 80% of the original value of the food's glycemic index.

The term "glycemic index" as used herein, is a number from 0 to 100 assigned to a food, with pure glucose assigned the value of 100, which represents the relative rise in the blood glucose level two hours after consuming that food. The glycemic index of a food is calculated by measuring the area under the curve (AUC) of a two-hour blood glucose response curve after ingestion of a food with a certain amount of carbohydrate following a 12-hour fast, dividing this value by the AUC of the standard (e.g. the same amount of glucose) and multiplying by 100. The glycemic index of a specific food depends on the quantity and type of carbohydrate it contains, but also on the amount of entrapment of the carbohydrate molecules within the food, as well as the efficiency of carbohydrate absorption. As defined herein, a food is considered to have a low glycemic index if it is 55 or less, a high glycemic index if it is 70 or more, and mid-range glycemic index if it is between 56 to 69.

The intestinal overlay formed by the compositions of the invention is transient and forms a short-term physical barrier which limits the absorption of nutrients and food particles in the GI tract, specifically in the small intestines.

In particular aspects, the physical barrier (i.e., intestinal overlay) formed by the compositions of the invention can be partial, discontinuous, discrete and spatially distributed, may have varying degrees of permeability, and may be present in varying amounts and regions of the GI tract. The physical barrier can include a bioadhesive component and may be delivered in the form of a syrup, a gel, a liquid, a powder, and combinations thereof. In particular embodiments, the intestinal overlay is non-absorbable and/or non-toxic, i.e. does not induce toxic effects because the polymeric material comprises a network formed only by interactions between the polymers present in the composition (food grade and pharmaceutical grade polymers), without participation of other chemical components.

In another aspect the present invention provided a method of maintaining or reducing the weight of a human subject to improve its bodily appearance, which method comprises administering to a subject in need an effective amount of a composition or formulation according to the invention. Furthermore, said method can assist in dealing with obesity and improve the bodily appearance of a subject by reduction of weight.

This invention disclosed herein relates to polymeric compositions characterized by the presence of at least two or more barrier-forming mucoadhesive substances as the primary active ingredient. The composition may further comprise additional components such as buffering agents, stabilizer, excipients, carriers, additives and the like. As used herein, the term "carrier" encompasses any of the standard carriers, such as a phosphate buffered saline solution, buffers, water, and emulsions, such as an oil/water or water/oil emulsion, and various types of wetting agents. The carrier also can include stabilizers and preservatives.

Additionally, plasticizers can be added to improve flexibility, flow, and reduce brittleness of the mucoadhesive film formed from the compositions disclosed herein.

Another primary aspect of the invention is that said compositions may comprise a component or more components, each of which may be selected from compounds and polymers detailed further herein and which some may serve as mucoadhesives and the like.

The terms "mucoadhesive" or "bioadhesive" as referred to herein may be described elsewhere in the art as binding or adhesive agents, which are employed in adhering to the mucosa of organs. In representative embodiments, the intestinal overlay formed by the compositions of the invention comprises a bioadhesive component. As used herein, the term "bioadhesive component" means any materials having adhesive properties which make them candidates for adhering to mucosa or mucins.

The term "barrier-forming mucoadhesive substance" as used herein is to be interpreted as synonymous to terms such as "layer-forming agent" or "film-forming agent", and denotes that such substance forms an overlay in the mucosa of the GI tract that behaves as a barrier (which is to be understood as a coat applied to the inner walls in the GI tract). This barrier may be gastro-resistant, gastro-protectant, or otherwise impermeable to certain nutrients. Examples of barrier-forming mucoadhesives may either prevent, block, protect, shield, cover, inhibit, reduce, lower, diminish, minimize, limit, restrict, suppress, remove, alter, manipulate, control, modulate, or regulate the contact, interaction, access, exposure, absorption, uptake, transport, transfer, permeation and diffusion of nutrients, food, food particles, sugars, fats, saccharides, glucose, lipids, fatty acids, proteins, amino acids, stomach acid, gastric acid, or gastric juice, in the GI tract.

The term "natural or synthetic hydrophilic molecules" as used herein, refers to molecules containing numerous organic functions that generate hydrogen bonds such as carboxyl, hydroxyl and amino groups, which do not adhere specifically onto several surfaces (e.g. carbomers, chitosans, alginates and cellulose derivatives). These polymers can be subdivided into three classes: cationic, anionic and nonionic.

The term "cationic molecules" as defined herein, refers to molecules that can interact with the mucus surface, since they are negatively charged at physiological pH, whereas, the term "anionic molecules" refers to molecules which are negatively charged and are also mucoadhesive due to physical-chemical processes such as hydrophobic interactions, hydrogen bonding and van der Waals bonds, which are controlled by the pH and the ionic composition.

The term "nonionic polymers" as defined herein refers to molecules that include hydroxypropyl methylcellulose, hydroxyethyl cellulose and methylcellulose, which present weaker mucoadhesion force compared to anionic polymers.

The composition according to the invention comprises at least two mucoadhesive substances, serving as the active ingredients, and can further comprise components selected from the groups of film-forming agents, natural or synthetic hydrophilic molecules, cationic molecules and/or anionic molecules, and nonionic polymers.

Importantly, the active ingredients of the compositions of the invention are selected from natural, synthetic or semi-synthetic monomers, oligomers or polymers including, but not limited to polysaccharides, ionic polymers, non-ionic polymers, derivatives, mixtures, blends, composites, cross-linked or interpenetrating networks thereof. The materials can appear in different molecular weight and from different sources (plants, synthetic, animals, etc.).

Specific examples of compounds, polymers and other materials useful according to the invention include, but are not limited to Carbopol®, cellulose, polycarbophil cysteine, poly (acrylic acid) derivatives, chemically modified poly (acrylic acids), polysaccharides, chitosan, chemically modified chitosan, cellulose, polycarbophil, cysteine, poly (acrylic acid), thiolated chitosan, poly(methacrylic acid) sodium salt, alginate, sodium carboxymethylcellulose, sodium hyaluronate, hydroxyethyl cellulose (HEC), hydroxypropyl cellulose (HPC), hydroxypropyl methylcellulose (HPMC), polyvinylpyrrolidone, polyethylene glycol (PEG), thiolated polymers, carboxymethylcellulose (CMC), dextran sulfate, hydroxyalkyl cellulose, dermatan sulfate, water soluble vinyl polymer, bismuth, guar gum, xanthan gum, gum karaya, pectin, hyaluronic acid (HA), tragacanth and combinations thereof.

Specific examples of bioadhesive materials used herein include chitosan, pectin, alginate, gum karaya, poly(ethylene glycol) (PEG), carboxymethyl cellulose (CMC), hyaluronic acid (HA), hydroxy ethyl cellulose (HEC), hydroxypropyl methylcellulose (HPMC), hydroxypropyl cellulose (HPC), guar gum, xanthan gum, tragacanth, carrageenan, carbopol (PAA), polycarbophyl.

Non-limiting examples of barrier-forming mucoadhesive formulations according to invention include: a formulation comprising chitosan and HEC; a formulation comprising chitosan and HPC; a formulation comprising chitosan and guar gum; a formulation comprising chitosan and alginate; a formulation comprising chitosan and gum karaya; a formulation comprising chitosan, pectin and alginate; a formulation comprising chitosan, CMC and PEG; a formulation comprising tragacanth, CMC, PEG and chitosan; a formulation comprising chitosan, HEC and alginate; a formulation comprising chitosan, HEC and guar gum; a formulation comprising chitosan, HEC, HPC, guar gum and alginate; a formulation comprising chitosan, HEC, HPC, guar gum, alginate and pectin; a formulation comprising chitosan, HEC, alginate and carbopol; a formulation comprising chitosan, HEC, HPC and carbopol; a formulation comprising chitosan, HEC, guar gum and carbopol; a formulation comprising alginate and HEC; a formulation comprising alginate and HPC; a formulation comprising alginate and guar gum; a formulation comprising HPC and carbopol; a formulation comprising HPC and guar gum; a formulation comprising pectin and gum karaya; a formulation comprising tragacanth and pectin; and a formulation comprising HPC and guar gum.

In some embodiments, the compositions of the invention further comprise one or more ingredients to protect the composition from pH-related degradation before the administration of said composition and/or after administration to a subject. Further, the compositions may also comprise one or more substances for achieving slow release of the composition, particular components thereof, or co-administered supplementary components.

The compositions and formulations of the invention comprising the bioadhesive substance remain in contact with the mucosal surface of the small intestines for a sufficient period of time for producing the desired effect, including time period ranging from 15 minutes to 7 days, including but not limited to from 1 hour to 3 hours, 1 hour to 12 hours, 1 hour to 24 hours, 1 to 3 days, or such as up to 1 hour, 5 hours, 12 hours, 24 hours, 2 days, 3 days, 4 days, 5 days, 6 days, or 7 days post administration, after which the intestinal overlay will fully or partially decompose and will be removed on its own or with additional components from one's gastrointestinal system.

According to a specific embodiment, the compositions and formulations of the invention remain in contact with the small intestinal surface for 1 to 36 hours post administration.

An important aspect of the invention is that after administering the composition to a subject, a coating that is incapable of being absorbed by the gut forms in situ on the inner walls of the GI tract, and specifically the small intestines (SI), which reduces the absorption of nutrients or, in addition, may allow other co-administered components, such as dietary supplements, to slowly release from the matrix to the GI and more specifically the SI for the purpose of absorption.

The term "incapable of being absorbed by the gut" is intended to mean that the polymeric material is not absorbed by the GI tract, and specifically the small intestine, for example via the transcellular or paracellular routes under normal physiological conditions. Instead, the polymeric material binds to the walls of the GI tract.

The present invention aims to significantly reduce the absorptive area of the small intestine by the creation of a physical barrier between the absorptive area and the chyme.

More specifically, the compositions of the invention are capable of adhering to SI surfaces by means of interaction between the mucoadhesive components of the compositions and the SI surfaces. These interactions may be physical, chemical, biochemical, via non-covalent bonding, covalent bonding, intermolecular bonding, cross-linking mechanism, self-assembly mechanism, silane-based mechanism.

After administering the compositions of the invention, they may come into contact with the surfaces of the SI by means of spraying, layering, depositing, self-assembly, constructing or otherwise forming a physical overlay.

The compositions of the invention form a physical barrier in situ along the inner walls of the GI tract, in length from about 1 cm to about 70 cm, including any value in between.

The compositions and formulations of the invention remain in contact with the small intestinal surface for a sufficient period of time for producing the desired effect, such as from 15 minutes to 7 days post administration, after which the intestinal overlay will fully or partially decompose and will be removed on its own or with additional components from one's gastrointestinal system.

Further, the compositions according to the invention may be formulated as liquid solutions, hydrogels (a material that swells in the presence of water) or capsules for single use.

In some embodiments, the SI surface is modified by orally administering a pill containing the composition which may be in various physical forms such as, but not limited to, powdered, blended, mixed, coated, micro- or nano-encapsulated, liquid, gel or hydrogel forms. The pill may have an enteric coating and in some embodiments the pill is a capsule. Furthermore, a pill capsule, tablet, osmotic delivery system (OROS), or a type of time release technology which comprises the disclosed compositions may also be orally administered.

In other embodiments, the composition is orally consumed as a liquid, emulsion, general beverage, extended release syrup, herbal tea or beverage, softgel, as powder, solution, suspension, syrup, concentrated or diluted syrup, orally disintegrating tablet (ODT), film or drug-film, confectionery such as a lollipop, sublingual drops, lozenges, effervescent buccal tablet, mouthwash, gel, chewing-gum, paste, ointment, oral spray, nanosphere suspension, insufflation, or mucoadhesive microdisc (microsphere tablet).

In some embodiments, the SI surface is modified by orally administering a liquid containing a single or multiple dissolved or suspended components, or may be in the form of a microsphere suspension, nanosphere suspension, emulsified, micro- or nano-encapsulated or dispersed by other means of the composition.

In some embodiments, the compositions or formulations of the invention may modify the SI surface via oral administration using per os (PO) techniques of a liquid or hydrogel or gel containing the composition or formulation.

In further embodiments, the compositions of the invention modifies the SI surface via a process comprising a sequential step of contacting the SI surface by the composition followed by modification of the SI surface by the composition. Said sequential steps may comprise chemical or physical interactions between components of the composition.

In some aspects, the SI overlay modulates the transport of all or some nutrients from the SI to the blood stream. The transport of nutrients from the SI cavity to the blood stream can be modulated by the physical barrier formed in situ between the SI cavity and SI surface by means of interactions between the SI overlay and SI surface. Said interactions between the SI surface modification and SI surface may be physical, chemical, or biochemical.

In some embodiments, the transportation of nutrients from the SI cavity to the blood stream is active, passive, or specific. Similarly, the blockage of nutrient transportation from the SI cavity to the blood stream is passive, active, or specific.

As used herein, the term "intestinal lumen" refers to the cavity of the intestines. Further, as used herein, the terms luminal contents or, more particularly, intraluminal contents should be understood to include chyme, alimentary flow, nutrients, and food particles inside the intestinal lumen.

As used herein, the term "proximal small intestines" should be understood to mean the portion of the intestines generally defined as the duodenum. Proximal small intestine should further be understood to include the first 0 to 50 cm of the small intestines following the stomach. That is, ranges such as the first 10 cm, the first 20 cm, the first 30 cm, and the first 40 cm of the human intestine should be included by proximal small intestines.

In particular embodiments, the physical barrier comprises a partial physical barrier. As used herein, the term "physical barrier" includes a structure that prevents the contact of one material with one or more other materials. For instance, a physical barrier may prevent the contact of the intraluminal contents (contents within the GI tract) with that of the lining and/or components within the wall of the GI tract. As used herein, the term "intestinal lining" refers to the lining of the wall of the GI tract which may comprise the mucosa and the mucus. Further, the term "partial" should be construed to mean less than 100%, discontinuous, discrete and spatially distributed, having varying degrees of permeability, or incomplete.

The physical barrier may be incomplete in preventing contact between one or more materials. Therefore, the physical barrier may further be partial, discontinuous, discrete and spatially distributed, may have varying degrees of permeability, and may be present in varying amounts and regions of the intestines. For instance, physical barrier may mean a semi-permeable liquid overlay in contact with the mucus or mucins of the intestines. In other embodiments of the present invention, physical barrier may refer to a plurality of discrete and spatially distributed amounts of material.

In some embodiments, the SI surface modification covers at least 1% of the SI surface and as much as 99% of the SI surface, including any value and range in between. The SI overlay may be continuous and or homogenous, discontinuous, or porous, where the thickness of the SI overlay can be nanometric, sub-micronic, or micronic.

As used herein, the terms "mucosa" or "mucosal surface" refer to the mucous membrane that provides a protective layer on the surface of the gastrointestinal (rectal, colon or intestinal).

In another embodiment, the invention provides a method of managing a person's weight comprising administering an effective amount of a composition comprising a barrier-forming mucoadhesive substance as defined above to a person. According to a particular embodiment, the composition forms a physical barrier in situ to limit an area of effective coverage on the lining of the GI tract to a section of the GI tract, for example a section that is less than about 30 cm in length, wherein the section of the intestines begin at the pyloric sphincter and extends distally toward the jejunum. In particular embodiments, the physical barrier that forms in the GI tract, may also start in the duodenum with, for example, progressively increasing lengths from about 1 cm to about 70 cm, including any value in between.

In some embodiments, the physical barrier is created when a cationic and/or cationic-anionic mixture compound combines in situ with the anionic mucins lining the wall of the intestines. As used herein, the term "creating in-situ" and variations thereof, implies enabling the formation of the final embodiment locally of the intended barrier from constituent elements at the desired site, rather than in a pre-assembled manner.

Notably, the compositions of the invention generate a transient barrier across the intestinal walls the coverage of which does not completely block the absorption of essential nutrients in the intestines, and therefore, these compositions are safe and do not pose a risk to a user in terms of malnourishment, vitamin and/or mineral deficiencies, and the like. The term "transient barrier" as used herein means a temporary or short-term physical barrier which lasts and causes the intended effect for the indicated time Furthermore, the skilled artisan will appreciate that composition disclosed herein can be modified to form an overlay in situ at one or more specific sites along the GI tract, such as the pyloric antrum, pyloric canal, and pyloric sphincter, pylorus, proximal small intestine, distal small intestine, duodenum, jejunum, ileum, cecum, portions of the large intestines or other parts of the GI tract of the person. In particular embodiments, the compositions of the invention form a barrier in situ in the proximal small intestine.

In certain embodiments, the compositions disclosed herein may form a barrier in the GI tract of the subject when contacted with an acidic substance or basic substance at a pH or range of pHs suitable for maintaining the physical barrier.

In certain embodiments, the composition comprising the bioadhesive component forms a physical barrier post administration having a thickness between about 0.1 microns and 1000 microns.

In some embodiments, the composition comprising the bioadhesive component forms a physical barrier comprising a component selected from the group consisting of a semi-permeable component, an impermeable component, and combinations thereof. In particular embodiments, the semi-permeable or impermeable layer has a thickness between about 0.1 microns and 1000 microns. The degree of composition's permeability can be determined in vitro as demonstrated in the Examples herein below, where, for example, glucose transport can serve as a indictor for permeability and can be described as blocked, partially blocked and pass with respect to the tested compositions.

The compositions of the invention can also exhibit one or more dimensions in the nano-scale or sub-micron-scale, such as nanostructures or nanoparticles, before or after administration of the composition to a person in need. As used herein, "nanoparticle", or "nanostructure" refers to a microscopic particle greater than 1 nanometer and less than about 1 micron in diameter.

In yet more particular embodiments, the physical barrier comprises an expandable hydrogel adapted to apply pressure on the inner intestinal lumen of the subject thereby facilitating adhesion of the physical barrier to the intestinal lumen.

The compositions may be prepared using one or more mixing techniques. For example, the composition may be prepared using high-shear mixing, homogenizing, sonication, and ultra-sonication, extruder, spray and freeze dry techniques.

In another embodiment, the components described herein are mixed at a temperature not less than 2° C. and not greater than 80° C. In another embodiment, the mixture is mixed for not less than 10 seconds and not greater than 90 minutes.

In some embodiments the compositions may be prepared using various surfactants and additives, and may be in the form of an oil-in-water (emulsion), water-in-oil (inverse emulsion), a solution, a suspension in aqueous media, a suspension in organic media, a nano-suspension in aqueous media, a nano-suspension in organic media, a dispersion in aqueous media, a dispersion in organic media, a nano-dispersion in aqueous media, a nano-dispersion in organic media, or it may be encapsulated in aqueous media, nano-encapsulated in aqueous media, encapsulated in organic media, or nano-encapsulated in aqueous media.

Furthermore, the compositions disclosed herein, when prepared in the form of an aqueous or organic solution, dispersion, nano-dispersion, suspension, or nano-suspension as described above may be dried via any number of processes which are known in the art (e.g. via freeze-drying, vacuuming, heating or altogether) to afford either a solid or dehydrated preparation.

All numerical designations, e.g., pH, temperature, time, concentration, and molecular weight, including ranges, are approximations which are varied (+) or (−) by increments of 0.1 or 1.0, as appropriate. It is to be understood, although not always explicitly stated, that all numerical designations are preceded by the term "about". It also is to be understood, although not always explicitly stated, that the reagents described herein are merely exemplary and that equivalents of such are known in the art.

As used in the specification and claims, the singular form "a", "an" and "the" include plural references unless the context clearly dictates otherwise.

"Comprising" refers to compounds, compositions and methods including the recited elements, but not excluding others. "Consisting essentially of," when used to define compounds, compositions or methods, shall mean excluding other elements that would materially affect the basic and novel characteristics of the claimed technology. "Consisting of," shall mean excluding any element, step, or ingredient not specified.

The term "SI surface modification" as used herein refers to a physical overlay formed by the compositions or formulations disclosed herein onto the inner surface of the GI tract, and specifically the small intestine, which modifies its absorption properties.

The term "in situ" as used herein means that the intended effect of the compositions or formulations disclosed herein occurs only once it has reached the desired or optimal position in the body and remains there as intended.

The terms "weight management" or "managing weight" as used herein, refers to both the techniques and underlying physiological processes that contribute to a person's ability to attain and maintain a certain weight. In the context of the instant invention, these terms include also the action of maintaining one's weight, weight-loss and even a reduction in weight gained when compared to that gained without the use of the compositions of the invention.

Some of the components used in the compositions of the invention may incorporate charged groups, which refers to a chemical functional group that is fully ionized resulting in that group having either a positive or a negative charge, or possibly multiple positive or multiple negative charges. For example, polymers could have multiple charged groups either as components of the polymer chain, and/or as attachments to the polymer, either direct attachment or by way of a linker. Polymer charged groups may be either naturally-occurring or synthetic. A charged group may be part of an active compound, either as an intrinsic component of that compound or as a synthetic analog of the active compound.

Furthermore, some of the components used in the compositions of the invention may incorporate an ionizable group, which refers to a chemical functional group that is partially ionized at or close to physiological pH resulting in that group having either a partial positive or a partial negative charge. The charge of an ionizable group will vary with pH. For example, polymers could have multiple ionizable groups either as components of the polymer chain, and/or as attachments to the polymer, either direct attachment or by way of a linker. Polymer ionizable groups may be either naturally-occurring or synthetic. An ionizable group may be part of an active compound, either as an intrinsic component of that compound or as a synthetic analog of the active compound.

In another embodiment of the invention, the composition may comprise a degradable polymer which can be broken down under specific conditions to smaller units. In one aspect, repeated degradation of the polymer units in situ (in the body) allows for small fragments to be excreted or otherwise eliminated. In another embodiment, the composition may comprise a stable polymer where its main structure (backbone) cannot be broken under conditions typically found in the body. In a stable polymer, it remains possible that functional groups attached to the polymer backbone can be modified or degraded under conditions typically found in the body. Non-limiting examples of such include, polyethers such as PEG, polyacrylates, and polymethacrylates.

As used herein, "nutraceutical" refers to a substance, polymer, compound, or mixtures thereof, that helps a person by providing or restricting nutrients that may otherwise be consumed in improper quantities.

As used herein, a "formulation" is a mixture of components containing one or more nutraceuticals provided in a viscous mucoadhesive liquid or mucoadhesive gel carrier suitable for administration to people. The formulation can be comprised of a single formulation for administration to a patient or comprised of two or more formulations that are brought together and mixed immediately prior to administration.

As used herein, "administer," "administering" or "administration" refers to the delivery of a nutraceutical formulation or composition of the invention to a person in a manner suitable for aiding the person in maintaining their weight. "Administration" can be effected in one dose, continuously or intermittently. Methods of determining the most effective means and dosage of administration are known to those of skill in the art and will vary with the composition used, the purpose, and the person who wishes to benefit from the invention.

The invention will now be described with reference to specific examples and materials. The following examples are representative of techniques employed by the inventors in carrying out aspects of the present invention. It should be appreciated that while these techniques are exemplary of specific embodiments for the practice of the invention, those of skill in the art, in light of the present disclosure, will recognize that numerous modifications can be made without departing from the spirit and intended scope of the invention.

EXAMPLES

Materials and Methods

Polymer Preparation

Alginate (sodium): alginate was dissolved at 5% w/v in DDW. The solution container was placed on a shaker for 20 minutes at 37° C. at 250 RPM.

Carbopol® (a high molecular weight cross-linked polyacrylic acid polymer): Carbopol® was added through sifter into DDW at 60° C. while stirring at 1400 RPM.

Carboxymethyl cellulose (CMC): CMC was dissolved at 1% w/v in DDW. The solution container was placed on a shaker for 20 minutes at 37° C. at 250 RPM.

Chitosan: chitosan was dissolved at 1-2% w/v in double-distilled water (DDW) containing acetic acid 1% (for 1% chitosan) or 2% (for 2% chitosan) v/v. The solution container was placed on a shaker for 10 minutes at 37° C. at 250 RPM.

Guar gum: guar gum was dissolved at 1% w/v in DDW. The solution container was placed on a shaker for 20 minutes at 37° C. at 250 RPM.

Gum Karaya (GK): GK was dissolved at 2.5% w/v in DDW. The solution container was placed on a shaker for 10 minutes at 37° C. at 250 RPM.

Hydroxyethyl cellulose (HEC): HEC was dissolved at 2% w/v in DDW. The solution container was placed on a shaker for 20 minutes at 37° C. at 250 RPM.

Hydroxypropyl cellulose (HPC): HPC was dissolved at 2.5% w/v in DDW. The solution container was placed on a shaker for 20 minutes at 37° C. at 250 RPM.

Hydroxypropyl methylcellulose (HPMC): HPMC was dissolved at 1% w/v in DDW. The solution container was placed on a shaker for 20 minutes at 37° C. at 250 RPM.

Pectin: apple pectin was dissolved at 1-2% w/v in DDW. The solution container was placed on a shaker for 20 minutes at 37° C. at 250 RPM.

Polyethylene glycol (PEG): PEG was dissolved at 30% w/v in DDW. The solution container was placed on a shaker for 10 minutes at 37° C. at 250 RPM Tragacanth: Tragacanth was dissolved at 2.5% w/v in DDW. The solution container was placed on a shaker for 20 minutes at 37° C. at 250 RPM.

Glucose Solution Preparation

Glucose (stock 45% solution, Sigma) was diluted in 1% acetic acid (AA) in DDW to obtain a final concentration of 0.1%. The solution was titrated by adding NaOH 1M until pH of ~6.0 was reached. Alternatively, phosphate-buffered saline (PBS) was prepared by dissolving 1.08 g $NaH_2PO_4$ and 0.1278 g $Na_2HPO_4$ in 1 L of DDW, and 1 g of D-glucose was added. pH of ~6.0 was verified.

10% glucose solution in PBS was prepared as described above, followed by the addition of 100 g D-glucose to 1 L solution. pH of ~6.0 was verified.

50% glucose solution for in vivo experiments was prepared by dissolving the desired amount of D-glucose in rats drinking water and then heating and stirring until the solution is clear and homogenous.

Evaluating the Blockage Efficacy Via Filtration Apparatus In Vitro

A 1 ml solution of 3% w/v porcine stomach mucin in DDW was evenly spread on a Whatman or nitrocellulose membrane using a pipette. The membrane was then incubated for 30 minutes at room temperature, followed by rinsing with DDW to remove excess of mucin. 1 ml of the indicated formulation was evenly spread on the mucin-coated membrane, using the K Hand coater starter kit, and the coated membrane was incubated again for 30 minutes at room temperature. Excess of reagents were rinsed using DDW. The coated membrane was placed on a vertical filtration apparatus. A solution containing 0.1% glucose was introduced to the filtration apparatus.

Successful blockage of glucose transport was defined as total blockage of the glucose solution (0.1%) penetration for up to 10 minutes, relative to control (mucin-coated membrane). Accordingly, three qualitative values were defined:

I) pass, i.e., fast penetration of liquid media through the membrane, within <30 seconds;
II) partly-blocked, i.e., liquid penetration only after the first 2 minutes; and
III) blocked, i.e., no liquid penetration for up to 10 minutes.

Evaluating the Blockage Efficacy Via Side-Bi-Side Diffusion Chamber In Vitro

Mucin- and formulation-coated nitrocellulose membranes were prepared as described above. The coated membrane was placed between the two diffusion cells of the side-bi side diffusion chamber. PBS containing glucose (10%) was introduced to the donor cell, while PBS (without glucose) was introduced to the acceptor cell. The diffusion chamber was incubated for 360 minutes (=6 hours) at 37° C. and 60 RPM. Samples were collected from the acceptor cell after 0, 30, 60, 120, 240 and 360 minutes. The volume withdrawn from the acceptor cell when sampling was replaces with fresh PBS. The donor cell was also sampled at t=0 and 360 minutes. Glucose levels were analyzed using HPLC and compared to the glucose levels in a control system, i.e., mucin-coated membrane, without formulation-coating.

Evaluating the Blockage Efficacy in Rats (In Vivo Model)

Sprague Dawley male Rats, with body weight of about 300 g to about 350 g were used. The rats were subjected to fasting for 7-15 hours, and then the barrier formulation (which was freshly prepared a day prior to use and kept at 37° C.) was administered by gavage at 1.0-2.0 ml per 100 grams body weight. 1 hour later, the rats were administered glucose solution (2-3 g/kg). Blood sampling was carried out by tail bleeding at times 0, 15, 30, 45, 60, 120, 150 and 180 minutes post glucose administration. Glucose levels in the blood were measured by a glucometer. Area under the curve (AUC) of blood glucose levels normalized to basal glucose levels was calculated for all treatment groups.

Example 1

Barrier Formulations are Safe for Use

Histology sections of the stomach and duodenum of untreated rats or rats treated with a formulation comprising chitosan (1.2% w/v), HEC (0.6% w/v) and alginate (0.5% w/v), that underwent homogenization (formulation 11.1) show that the coating of the stomach and duodenum with the barrier formulation tested did not exert any abnormalities or side effects to the tissues.

Example 2

Glucose Transport in an In Vitro Filtration System was Blocked by Coating a Membrane with a Barrier Formulation As a preliminary screening, various formulations were tested for their glucose transport inhibition properties in a filtration system using a mucin-coated membrane that was also coated with the formulations. The evaluation of the barrier properties of the formulations was performed by introducing a solution containing glucose to one side of the coated membrane and quantitating the amount of glucose that passed through the membrane. Three qualitative values were defined: (I) pass, i.e., fast penetration of liquid media through the membrane, within <30 seconds; (II) partly blocked, i.e., liquid penetration only after the first 2 minutes; and (III) blocked, i.e., no liquid penetration for up to 10 minutes. The results are summarized in Table 1.

TABLE 1

Evaluation of glucose transport through a coated membrane in a filtration system

| Formulation | Ingredients (Final Conc. % w/v) | Glucose Transport |
|---|---|---|
| F1 | Chitosan (0.05) + alginate (2.5) | Blocked |
| F2 | Chitosan (1) + alginate (0.5) | Partly blocked |
| F3 | Chitosan (1.5) + gum karaya (0.25) | Partly blocked |
| F4 | Chitosan (0.075) + alginate (1.25) | Blocked |
| F5 | Chitosan (0.9) + pectin (0.1) + alginate (0.25) | Pass |
| F6 | Chitosan (1.8) + pectin (0.1) + alginate (0.25) | Partly blocked |
| F7 | Pectin (1) + gum karaya (0.5) | Pass |
| F8 | Tragacanth (1.65) + pectin (0.66) | Pass |
| F9 | Chitosan (1.2) + CMC (0.3) + PEG 20 kDa (3) | Partly blocked |
| F10 | Tragacanth (1) + CMC (0.25) + HPC (0.625) + chitosan (0.2) | Pass |
| F11 | Chitosan (1.2) + HEC (0.6) + alginate (0.5) | Blocked |
| F12 | Chitosan (1.2) + HEC (0.6) + guar gum (0.1) | Blocked |
| F13 | Chitosan (1) + HEC (0.4) + HPC (0.5) + guar gum (0.09) + alginate (0.05) | Blocked |
| F14 | Chitosan (0.8) + HEC (0.4) + HPC (0.5) + guar gum (0.1) + alginate (0.1) + pectin (0.16) | Blocked |
| F15 | Chitosan (1) + HEC (0.3) + HPC (0.375) + guar gum (0.1) + alginate (0.5) | Blocked |
| F17 | Chitosan (1.08) + HEC (0.54) + alginate (0.45) + carbopol (0.1) | Blocked |
| F18 | Chitosan (1) + HEC (0.4) + HPC (0.5) + carbopol (0.1) | Blocked |
| F19 | Chitosan (1.08) + HEC (0.54) + guar gum (0.09) + carbopol (0.1) | Partly blocked |

Example 3

Glucose Transport in an In Vitro Diffusion Chamber was Blocked by Coating a Membrane with a Single Polymer The level of glucose transport inhibition was evaluated in an in vitro model comprising side-bi-side diffusion chamber. A mucin- and polymer-coated membrane was placed in the diffusion chamber between a donor cell containing glucose solution and the acceptor cells containing glucose-free solution. Samples from the acceptor cells were taken at 0, 30, 60, 120, 240 and 360 minutes of incubation and glucose levels in the solution were analyzed. The tested polymers are listed on Table 2.

TABLE 2

List of tested single polymers

| Polymer No. | Polymer Name |
|---|---|
| P1 | Chitosan |
| P2 | Pectin |
| P3 | Alginate |
| P4 | Gum karaya |
| P5 | Polyethylene glycol (PEG) |
| P6 | Carboxymethyl cellulose (CMC) |
| P7 | Hyaluronic acid (HA) |
| P8 | Hydroxy ethylcellulose (HEC) |
| P9 | Hydroxypropyl methylcellulose (HPMC) |
| P10 | Hydroxypropyl cellulose (HPC) |
| P11 | Tragacanth |
| P12 | Guar gum |
| P13 | Xanthan gum |
| P15 | Carbopol ® |

During the first 30 minutes, the tested polymers showed between about 20% to about 60% glucose transport inhibition. Eleven of the tested polymers exhibited minimal to short-term (up to 2 hours) inhibition of glucose transport. However, the polymers chitosan, alginate, xanthan gum and Carbopol® maintained their inhibitory effect on glucose transport throughout the 6 hours experiment.

In order to improve the efficacy of the materials, formulations comprising at least two polymers were tested.

Example 4

Glucose Transport in an In Vitro Diffusion Chamber was Blocked by Coating a Membrane with a Polymer Pair Formulation In another experiment, some polymers that exhibited better inhibition results in terms of level and duration were tested as mix of two polymers. The tested polymer pairs are listed on Table 3.

TABLE 3

List of tested polymer pairs

| Polymer Pair No. | Ingredients (Final Conc. % w/v) |
|---|---|
| PP1 | Chitosan (1) + HEC (1) |
| PP2 | Alginate (2.5) + HEC (1) |
| PP3 | Alginate (2.5) + HPC (1.25) |
| PP4 | Alginate (2.5) + guar gum (0.5) |
| PP5 | HPC (1.25) + carbopol ® (0.5) |
| PP6 | HPC (1.25) + guar gum (0.5) |
| PP7 | Chitosan (1) + HPC (1.25) |
| PP8 | Chitosan (1) + guar gum (0.5) |
| PP9 | HEC (1) + HPC (1.25) |
| PP10 | HEC (1) + guar gum (0.5) |

Figure 2:
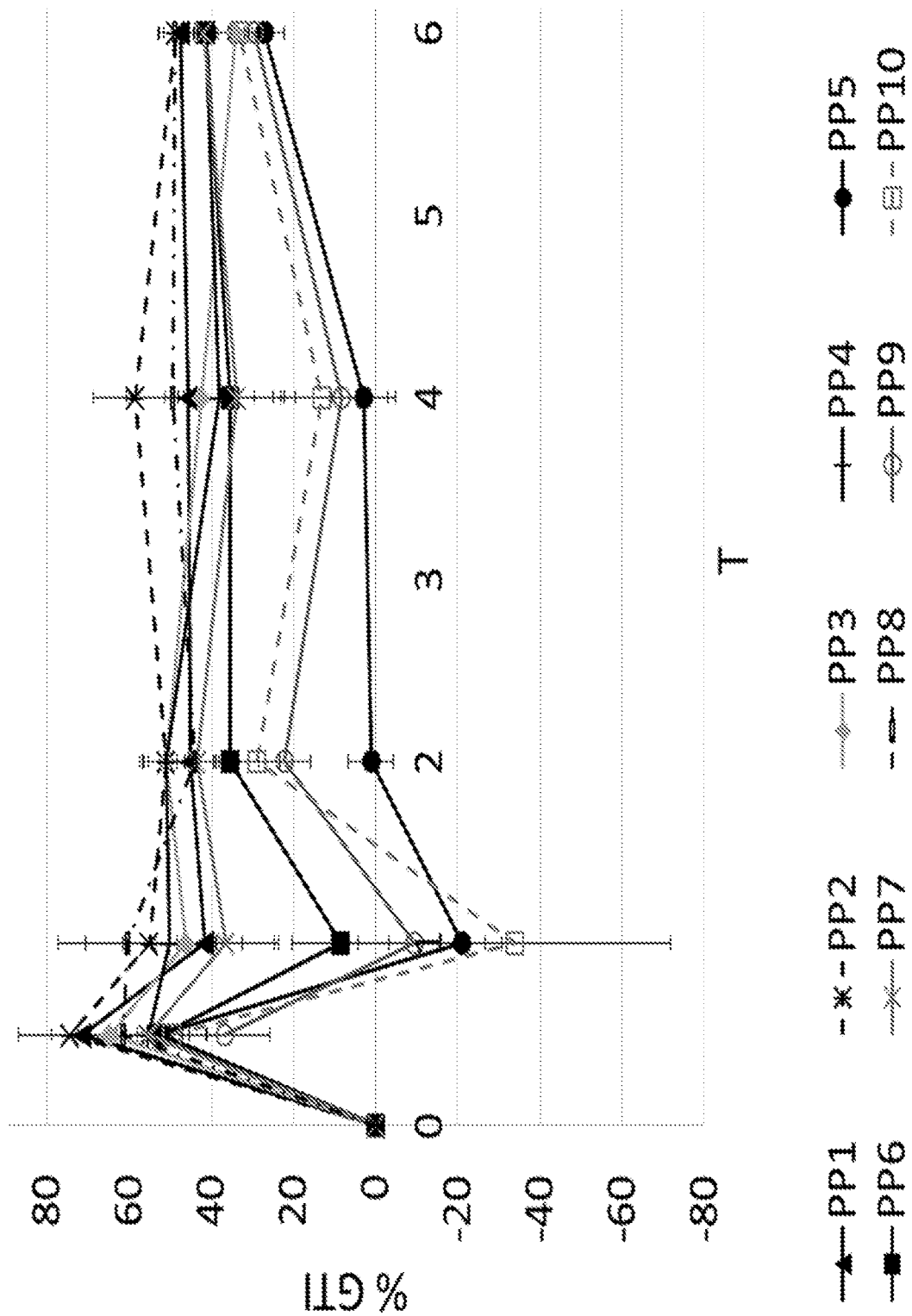
FIG. 2 shows percent of glucose transport inhibition (GTI) over time (T, in hours) in a side-bi-side diffusion chamber through a mucin-coated membrane further coated with the indicated polymer pair (PP) compared to a reference mucin-coated membrane. Polymer pair composition is as described in Table 3 below.

FIG. 2 shows the different kinetics of each of the teste polymer pair during 6 hours of incubation. Polymer pairs PP1, PP2, PP3, PP4, PP7 and PPB, exhibited a relatively constant level of glucose transport inhibition of at least about 40%.

Example 5

Glucose Transport in an In Vitro Diffusion Chamber was Blocked by Coating a Membrane with a Barrier Formulation In another in vitro model, side-bi-side diffusion chamber was used to evaluate in vitro the glucose transport inhibition properties of selected formulations. A mucin- and formulation-coated membrane was placed in the diffusion chamber between a donor cell containing glucose solution and the acceptor cells containing glucose-free solution. Samples from the acceptor cells were taken at 0, 30, 60, 120, 240 and 360 minutes of incubation and glucose levels in the solution were analyzed.

The side-bi-side diffusion platform exhibited good and fast indication for glucose transport through the coated-membrane, simulating the walls of the small intestine (SI).

As shown in FIG. 3, all the tested formulations led to a significant reduction in glucose transport compared to control mucin-coated membrane during the first 30 minutes of the experiment. Formulation 17.1 (comprising the ingredients as specified in Table 3 and further subjected to homogenization) maintained a relatively stable inhibition levels of over 40% after the first hour of the experiment. Formulations 11.1, 12.1, 13.1, 14.1, 15.1 and 18.1 showed fluctuations in the glucose transport inhibition of between about 10% and about 45%.

Overall, all the tested formulations exhibited strong and significant reduction of glucose transport during at least 6 hours of glucose sampling. The side-bi-side diffusion chamber was demonstrated as an important tool for quick and reliable evaluation for a formulation's efficacy in inhibiting transport of materials through barriers.

Example 6

Glucose Transport was Blocked by Coating the SI of Rats In Vivo

Glucose transport inhibition was also examined in-vivo in rats, which were administered with a barrier formulation, followed by a glucose solution. Glucose blood levels were measured at several time points.

Figure 4A:
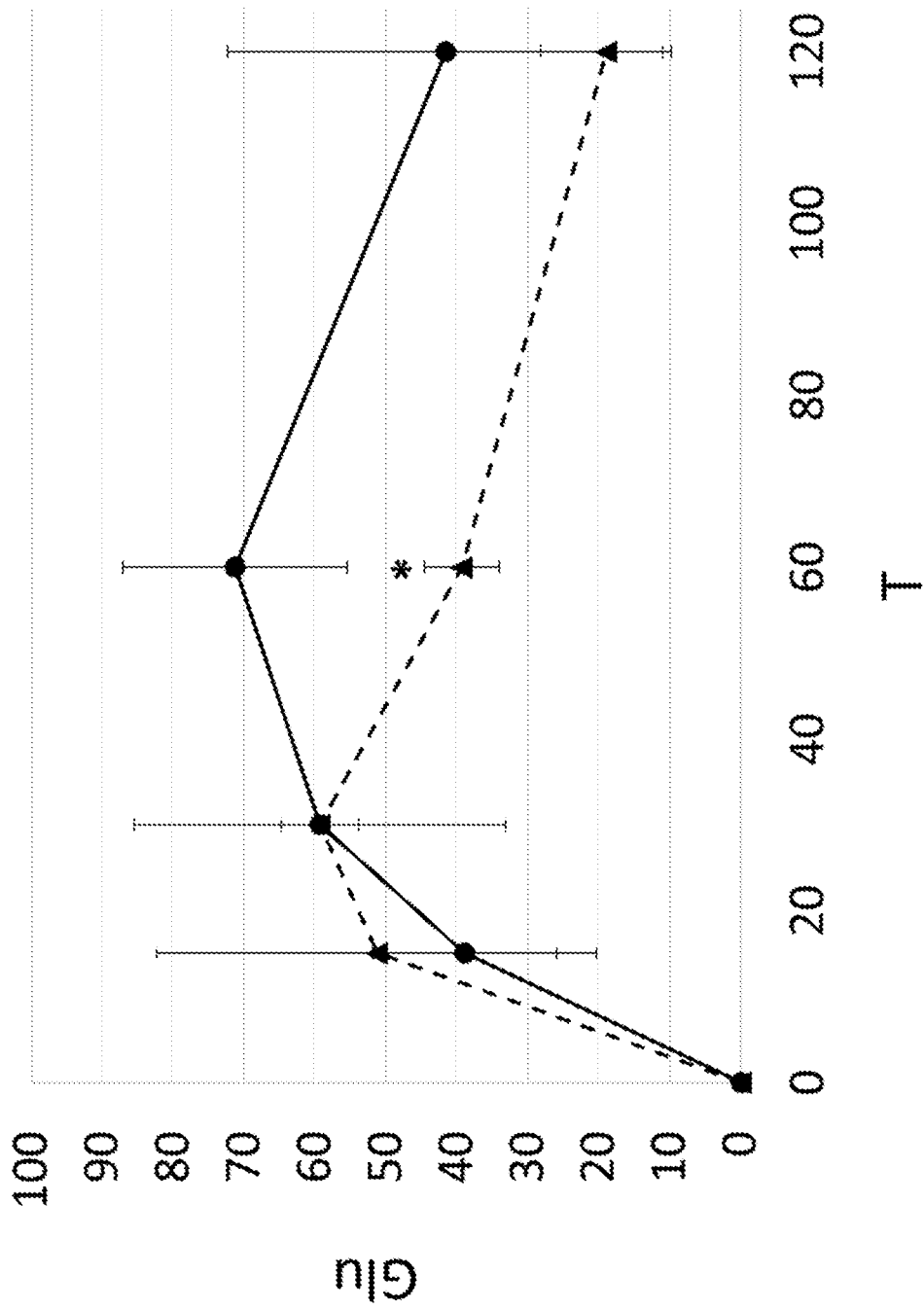
FIGS. 4A-4B show blood glucose levels in rats treated with a barrier solution and administered glucose thereafter.

As shown in FIG. 4A, the animals treated with formulation 13 exhibited reduced glucose peak. In addition, as shown in Table 4A, the treated animals exhibited a 32% reduction in the area under the curve (AUC) compared to control group, indicating that nutrients adsorption in the small intestine was partially blocked.

TABLE 4A

AUC of blood glucose levels normalized to basal glucose levels in control rats and rats treated with formulation 13

| Treatment | AUC (mg/dL × min) | Difference (%) |
| --- | --- | --- |
| Control | 7255 | 32 |
| Formulation 13 | 4965 | |

Figure 4B:
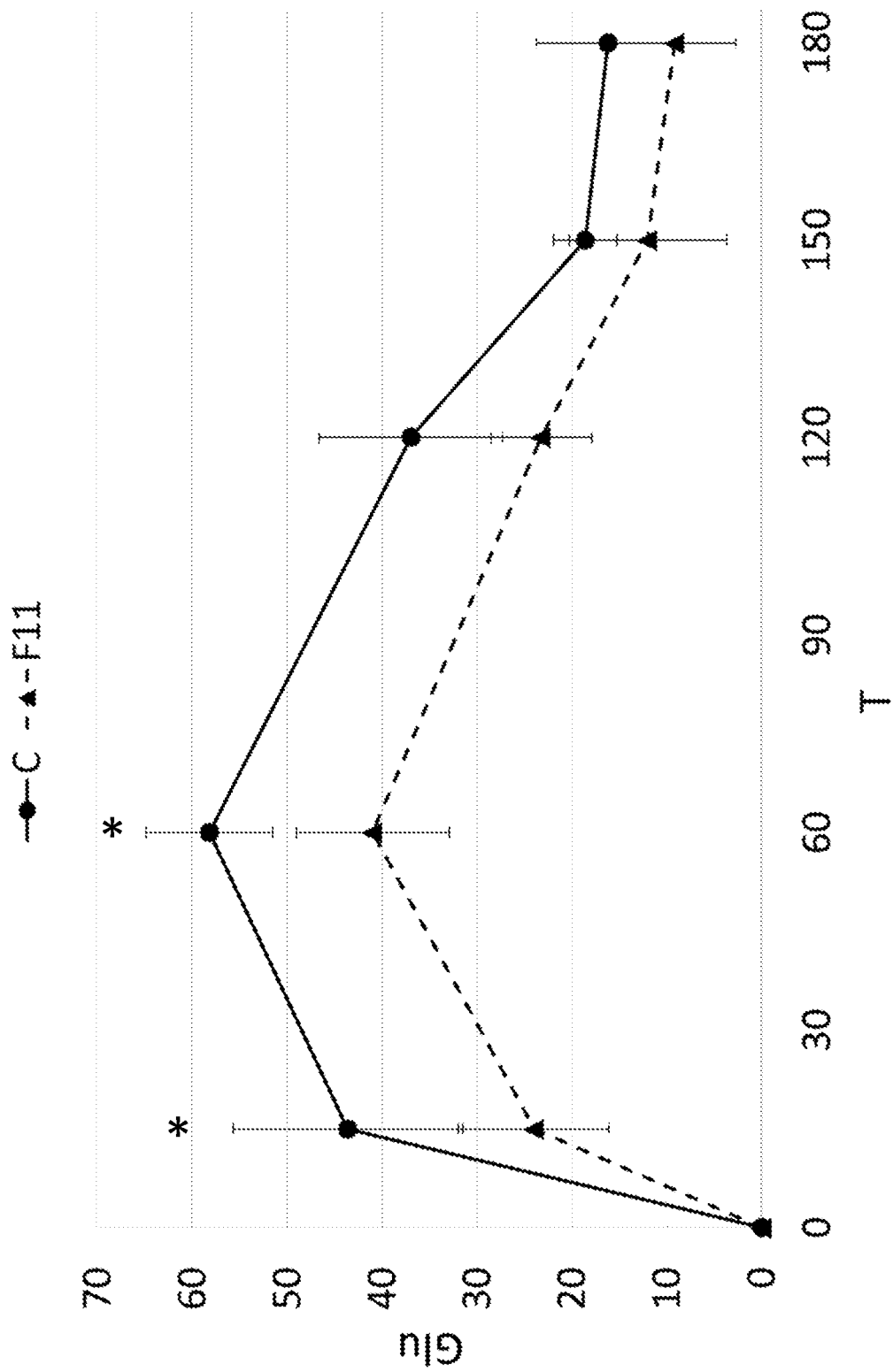

Furthermore, as shown in FIG. 4B, rats treated with formulation 11 also exhibited a marked reduction in the glucose peak than untreated rats. The area under the curve (AUC) for the group treated with formulation 11 was smaller by about 35% compared to control group, as presented in Table 4B.

TABLE 4B

AUC of blood glucose levels normalized to basal glucose levels in control rats and rats treated with formulation 11

| Treatment | AUC (mg/dL × min) | Difference |
| --- | --- | --- |
| Control | 6830 | (%) |
| Formulation 11 | 4415 | 35.4 |

The invention claimed is:

1. A composition comprising two or more barrier-forming mucoadhesive substances as active ingredients, said mucoadhesive substances producing an intestinal overlay when consumed by a person for use in managing the weight of said person,
said composition formulated as a liquid and comprising chitosan at 1.2% w/v, hydroxy ethyl cellulose at 0.6% w/v and alginate at 0.5% w/v.

2. The composition according to claim 1, formulated to reduce the absorption of nutrients and food particles in the gastrointestinal (GI) tract.

3. The composition according to claim 2, wherein said nutrients and food particles comprise proteins, amino acids, sugars, glucose, fats, fatty acids, and lipids.

4. The composition according to claim 1, formulated to form a temporary physical barrier which limits the absorption of nutrients and food particles in the small intestines.

5. The composition according to claim 4, wherein said temporary physical barrier remains in contact with the mucosal surface of the small intestines for a time period ranging from 15 minutes to 7 days post administration.

6. The composition according to claim 2, formulated to reduce the glycemic index of nutrients and food particles by at least 10% and up to 80% of the original glycemic index value.

7. A method of managing the weight of a person comprising administering to said person an effective amount of a composition according to claim 1.

8. The method according to claim 7, wherein managing the weight of a person includes reducing the absorption of nutrients and food particles in the gastrointestinal (GI) tract.

9. The method according to claim 8, wherein said nutrients and food particles comprise sugars.

10. The method according to claim 7, wherein the composition is administered intermittently.

11. The method according to claim 7, wherein said administering occurs before a meal.

12. The method according to claim 7, wherein said person is an individual interested in attaining or maintaining a certain body weight.

13. The method according to claim 7, wherein said person is one with a BMI that is 25 or more.

14. The method according to claim 8, wherein the method conforms to a person's lifestyle or eating habits.

\* \* \* \* \*